United States Patent
Wu et al.

(10) Patent No.: US 10,215,714 B1
(45) Date of Patent: *Feb. 26, 2019

(54) METHOD AND SYSTEM FOR DETECTING DEFECTS ON SURFACE OF OBJECT

(71) Applicant: Siemens Energy, Inc., Orlando, FL (US)

(72) Inventors: Ziyan Wu, Plainsboro, NJ (US); Rameswar Panda, Riverside, CA (US); Jan Ernst, Plainsboro, NJ (US); Kevin P. Bailey, Chuluota, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 6 days.

This patent is subject to a terminal disclaimer.

(21) Appl. No.: 15/678,335

(22) Filed: Aug. 16, 2017

(51) Int. Cl.
| | |
|---|---|
| *G06K 9/46* | (2006.01) |
| *G06T 7/00* | (2017.01) |
| *G01N 21/956* | (2006.01) |
| *G06T 7/33* | (2017.01) |

(52) U.S. Cl.
CPC ......... *G01N 21/956* (2013.01); *G06K 9/4661* (2013.01); *G06T 7/001* (2013.01); *G06T 7/0006* (2013.01); *G06T 7/33* (2017.01)

(58) Field of Classification Search
CPC . G06T 7/0004; G06T 7/11; G06T 5/30; G06T 5/50; G06K 9/6256; G06K 9/6267
See application file for complete search history.

(56) References Cited

U.S. PATENT DOCUMENTS

| | | | | |
|---|---|---|---|---|
| 5,828,778 A | * | 10/1998 | Hagi | G06T 7/0004 382/145 |
| 5,917,935 A | * | 6/1999 | Hawthorne | G02F 1/1303 348/126 |
| 2003/0160627 A1 | * | 8/2003 | Muradian | G01N 21/95607 702/117 |
| 2004/0146295 A1 | * | 7/2004 | Furman | G01N 21/8806 398/9 |
| 2006/0181700 A1 | * | 8/2006 | Andrews | G01N 21/21 356/237.2 |

(Continued)

OTHER PUBLICATIONS

Skumanich et al, "CMP process development based on rapid automatic defect classification", 1999, Proc. SPIE 3743, In-Line Characterization, Yield Reliability, and Failure Analyses in Microelectronic Manufacturing, 14 pages (Year: 1999).*

*Primary Examiner* — David F Dunphy

(57) ABSTRACT

Method and system for detecting defects on surface of object are presented. An imaging device captures images of surface of object under ambient and dark field illumination conditions. The images are processed with a plurality of image operations to detect area of potential defect at location on surface of object based on predictable pattern consisting of bright and shadow regions. Kernels are defined corresponding to configurations of dark field illumination sources to enhance detecting potential defect. Areas of potential defect are cut from processed images to sub images. Sub images are stitched together to generate hypothesis of potential defect at location on surface of object. The hypothesis is classified with a classifier to determine whether the potential defect is true defect. The classifier is trained with training data having characteristics of true defect. The method provides efficient automated detection of micro defects on surface of object.

20 Claims, 3 Drawing Sheets

(56) References Cited

U.S. PATENT DOCUMENTS

| | | | |
|---|---|---|---|
| 2009/0028423 A1* | 1/2009 | Sandstrom | G01N 21/956 |
| | | | 382/149 |
| 2013/0277553 A1* | 10/2013 | Otani | G01N 21/8806 |
| | | | 250/307 |
| 2013/0306615 A1* | 11/2013 | Rozbicki | G02F 1/153 |
| | | | 219/219 |
| 2017/0085760 A1 | 3/2017 | Ernst et al. | |
| 2018/0188188 A1* | 7/2018 | Zhao | G01N 21/8806 |

* cited by examiner

METHOD AND SYSTEM FOR DETECTING DEFECTS ON SURFACE OF OBJECT

TECHNICAL FIELD

This invention relates generally to a method and a system for detecting a defect on a surface of an object.

DESCRIPTION OF RELATED ART

Defect detection is an important aspect of industrial production quality assurance process which may provide an important guarantee for quality of products. Defects may be cracks on a surface of an object. Defects may be very small. Scale of the defects may be as small as micrometers.

Traditional methods of micro defect detection involve significant manual process which may not guarantee consistent quality of detection. Due to small scale of the micro defects, it may require a considerably long detection time to achieve certain accuracy using traditional methods. Some traditional detection methods may require applying certain chemicals which may damage the object. Methods currently being used in industry for detecting defects on surface of object are time consuming and may not provide consistent quality of detection.

SUMMARY OF INVENTION

Briefly described, aspects of the present invention relate to a method and a system for detecting a defect on a surface of an object.

According to an aspect, a method for detecting a defect on a surface of an object is presented. The method comprises supporting the object on a platform. The method comprises illuminating the surface of the object with a plurality of illumination sources comprising at least one ambient illumination source and at least one dark field illumination source. The method comprises capturing images of the surface of the object under illumination conditions with the illumination sources using an imaging device. The method comprises processing the captured images with a plurality of image operations using an image processor to detect an area of a potential defect at a location on the surface of the object. The method comprises cutting the area of the potential defect from the processed images to sub images using the image processor. The method comprises stitching the sub images together to generate a hypothesis of the potential defect at the location on the surface of the object using the image processor. The method comprises classifying the hypothesis in the stitched image with a classifier to determine whether the potential defect is a true defect using the image processor. The classifier is trained with training data having characteristics of the true defect. The method comprises generating an output of the classification comprising the detected true defect and the location on the surface of the object.

According to an aspect, a system for detecting a defect on a surface of an object is presented. The system comprises a platform for supporting the object. The system comprises a plurality of illumination sources comprising at least one ambient illumination source and at least one dark field illumination source for illuminating the surface of the object. The system comprises an imaging device for capturing images of the surface of the object under illumination conditions with the illumination sources. The system comprises an image processor. The image processor processes the captured images with a plurality of image operations using to detect an area of a potential defect at a location on the surface of the object. The image processor cuts the area of the potential defect from the processed images to sub images. The image processor stitches the sub images together to generate a hypothesis of the potential defect at the location on the surface of the object. The image processor classifies the hypothesis in the stitched image with a classifier to determine whether the potential defect is a true defect. The classifier is trained with training data having characteristics of the true defect. The image processor generates an output of the classification comprising the detected true defect and the location on the surface of the object.

According to an aspect, a computer program executable in a computer for performing a method of detecting a defect on a surface of an object is presented. The computer stores images of the surface of the object under illumination conditions with illumination sources comprising at least one ambient illumination source and at least one dark field illumination source. The method comprises step of processing the images with a plurality of image operations to detect an area of a potential defect at a location on the surface of the object. The method comprises step of cutting the area of the potential defect from the processed images to sub images. The method comprises step of stitching the sub images together to generate a hypothesis of the potential defect at the location on the surface of the object. The method comprises step of classifying the hypothesis in the stitched image with a classifier to determine whether the potential defect is a true defect. The classifier is trained with training data having characteristics of the true defect. The method comprises step of generating an output of the classification comprising the detected true defect and the location on the surface of the object.

Various aspects and embodiments of the application as described above and hereinafter may not only be used in the combinations explicitly described, but also in other combinations. Modifications will occur to the skilled person upon reading and understanding of the description.

BRIEF DESCRIPTION OF DRAWINGS

Exemplary embodiments of the application are explained in further detail with respect to the accompanying drawings. In the drawings.

To facilitate understanding, identical reference numerals have been used, where possible, to designate identical elements that are common to the figures.

DETAILED DESCRIPTION OF INVENTION

A detailed description related to aspects of the present invention is described hereafter with respect to the accompanying figures.

Figure 2:
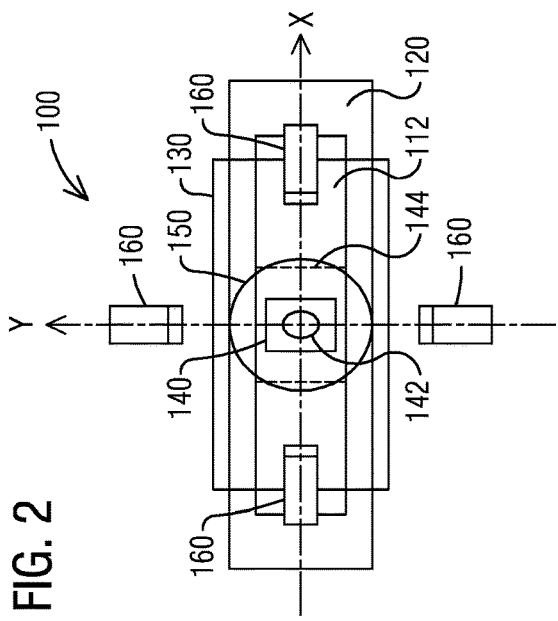
FIG. 2 illustrates a schematic top view of a system for detecting a defect at a surface of an object according to an embodiment of the invention.
Figure 1:
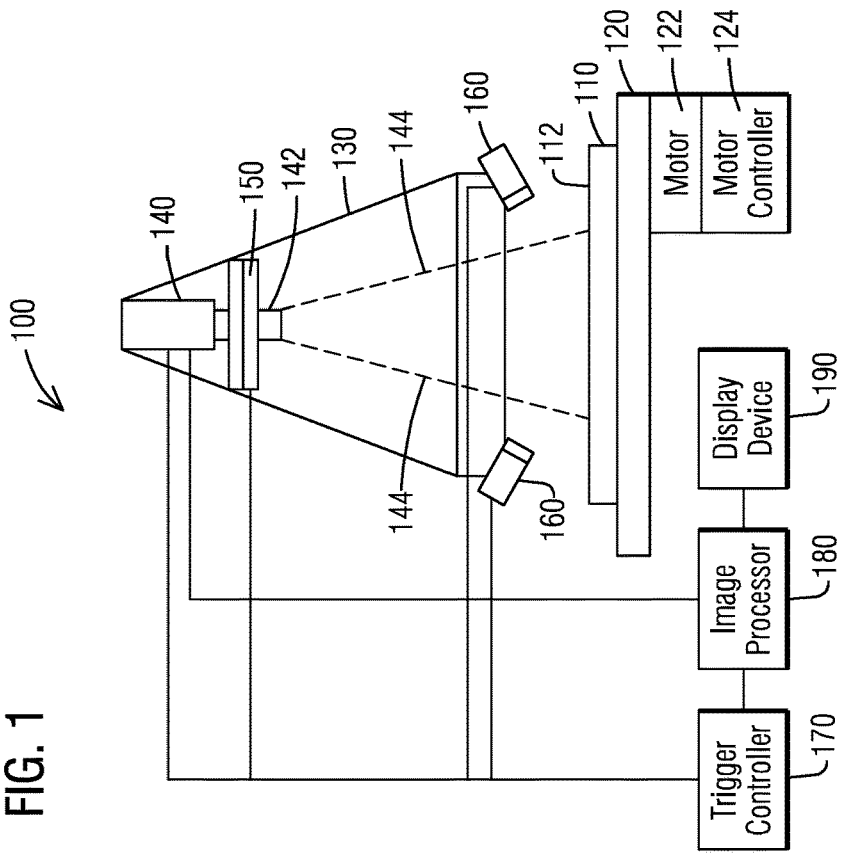
FIG. 1 illustrates a schematic side view of a system for detecting a defect at a surface of an object according to an embodiment of the invention.

FIGS. 1 and 2 respectively illustrate a schematic side view and top view of a system 100 for detecting a defect at a surface 112 of an object 110 according to an embodiment of the invention. The system 100 may include a platform 120 that supports the object 110. The system 100 may include a motor 122. The platform 120 may be movable along at least one direction by the motor 122. The motor 122 may have a motor controller 124 that controls a movement of the platform 120.

The system 100 may include a hood 130 arranged above the platform 120. The hood 130 may have a hollow cone shape. The system 100 may have an imaging device 140. The imaging device 140 may be arranged inside the hood 130. The imaging device 140 may be located at top of the hood 130. The imaging device 140 may include, for example, a camera. The imaging device 140 may include a lens 142. The lens 142 may be arranged at a location relative to the surface 112 of the object 110 such that the imaging device 140 may have a desirable field of view 144 on the surface 112 of the object 110. The imaging device 140 may pan and tilt relative to the surface 112 of the object 110 to achieve a desired field of view 144 on the surface 112 of the object 100. The motor 122 may move the platform 120 along with the object 110 so that the field of view 144 of the imaging device 140 may cover different areas of the surface 112 of the object 110.

The system 100 may have at least one ambient illumination source 150. The ambient illumination source 150 may be arranged inside the hood 130. The ambient illumination source 150 may be located at top of the hood 130. The ambient illumination source 150 may provide an ambient illumination condition at the surface 112 of the object 110. The ambient illumination source 150 may include, for example, a light emitting diode (LED) strobe light. The ambient illumination source 150 may have a ring shape. According to an exemplary embodiment as illustrated in FIG. 1, the lens 142 may extend through the ring shaped ambient illumination source 150.

The system 100 may include at least one dark field illumination source 160. The dark field illumination source 160 may be arranged at bottom of the hood 130. The dark field illumination source 160 may provide a dark field illumination condition on the surface 112 of the object 110. The dark field illumination source 160 may include, for example, a LED strobe light. The dark field illumination source 160 may be oriented at a location relative to the surface 112 of the object 110 such that a dark field illumination condition may be provided within the field of view 144 of the lens 142 at the surface 112 of the object 110. Under a dark field illumination condition, a defect may have a predictable pattern consisting of a bright region that is illuminated by the dark field illumination source 160 and a dark or shadow region that is not illuminated by the dark field illumination source 160.

With reference to FIG. 2 which illustrates a schematic top view of the system 100, four dark field illumination sources 160 are arranged at bottom of the hood 130. Two dark field illumination sources 160 are arranged along an x-axis in a plane of the field of view 144. The two dark field illumination sources 160 are located at two sides of the field of view 144 respectively, denoted x-positive and x-negative. Two other dark field illumination sources 160 are arranged along a y-axis in the plane of the field of view 144. The two other dark field illumination sources 160 are located at two sides of the field of view 144 respectively, denoted y-positive and y-negative. Different numbers of dark field illumination sources 160 may be arranged at bottom of the hood 130.

With reference to FIG. 1, the system 100 may include a trigger controller 170. The trigger controller 170 may functionally connect to the imaging device 140, the ambient illumination source 150 and the dark field illumination sources 160. The trigger controller 170 may trigger the ambient illumination source 150 and the dark field illumination sources 160 at a defined pattern, sequence, or simultaneously. The trigger controller 170 may trigger the imaging device 140 to capture images of the surface 112 of the object 110 under the triggered illumination conditions respectively. The trigger controller 170 may control configurations of the dark field illumination sources 160. The configurations of the dark field illumination sources 160 may include orientations of the dark field illumination sources 160 relative to the surface 112 of the object 110, illumination intensities of the dark field illumination sources 160, etc. According to an embodiment, the trigger controller 170 may be a computer having a computer program implemented.

The system 100 may include an image processor 180. The image processor 180 may functionally connect to the imaging device 140. The images captured by the imaging device 140 may be stored in the image processor 180. The image processor 180 may also process the images captured by the imaging device 140 to detect defects on the surface 112 of the object 110. According to an embodiment, the image processor 180 may be a computer. A computer program is executable in the imaging processor 180. According to an embodiment, the trigger controller 170 and the image processor 180 may be integrated parts of one computer. The system 100 may include a display device 190 functionally connected to the imaging processor 180. The display device 190 may display the captured images. The display device 190 may display the processed images. The display device 190 may display an output including information of a detected defect. The display device 190 may be a monitor. The display device 190 may be an integrated part of the imaging processor 180.

Figure 3:
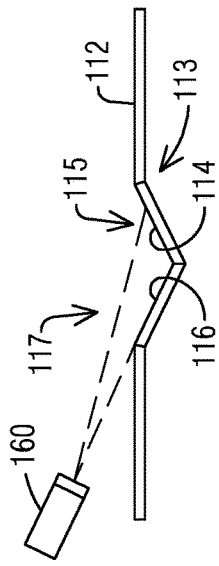
FIG. 3 illustrates a schematic diagram of a pattern consisting of a bright region and a shadow region of a defect on a surface under a dark field illumination source according to an embodiment of the invention.

According to an embodiment, a shape of a potential defect, such as size or length of the defect, may have a specific and predictable pattern consisting of bright region and shadow region in an image under different configurations of the dark field illumination sources 160. FIG. 3 illustrates a schematic diagram of a pattern consisting of a bright region 115 and a shadow region 117 of a defect 113 on a surface 112 under a dark field illumination source 160 according to an embodiment. As illustrated in FIG. 3, a surface 112 may have a V-shaped defect 113. A first portion 114 of the V-shaped defect 113 is illuminated by the dark filed illumination source 160 that forms a bright region 115 in an image. A second portion 116 of the V-shaped defect 113 is not illuminated by the dark filed illumination source 160 that forms a shadow region 117 in the image. The bright region 115 and the shadow region 117 are within a field of view 144 of an imaging device 140. The V-shaped defect 113 may be a micro defect, for example, scale of the V-shaped 113 defect may be as small as micrometers.

Figure 4:
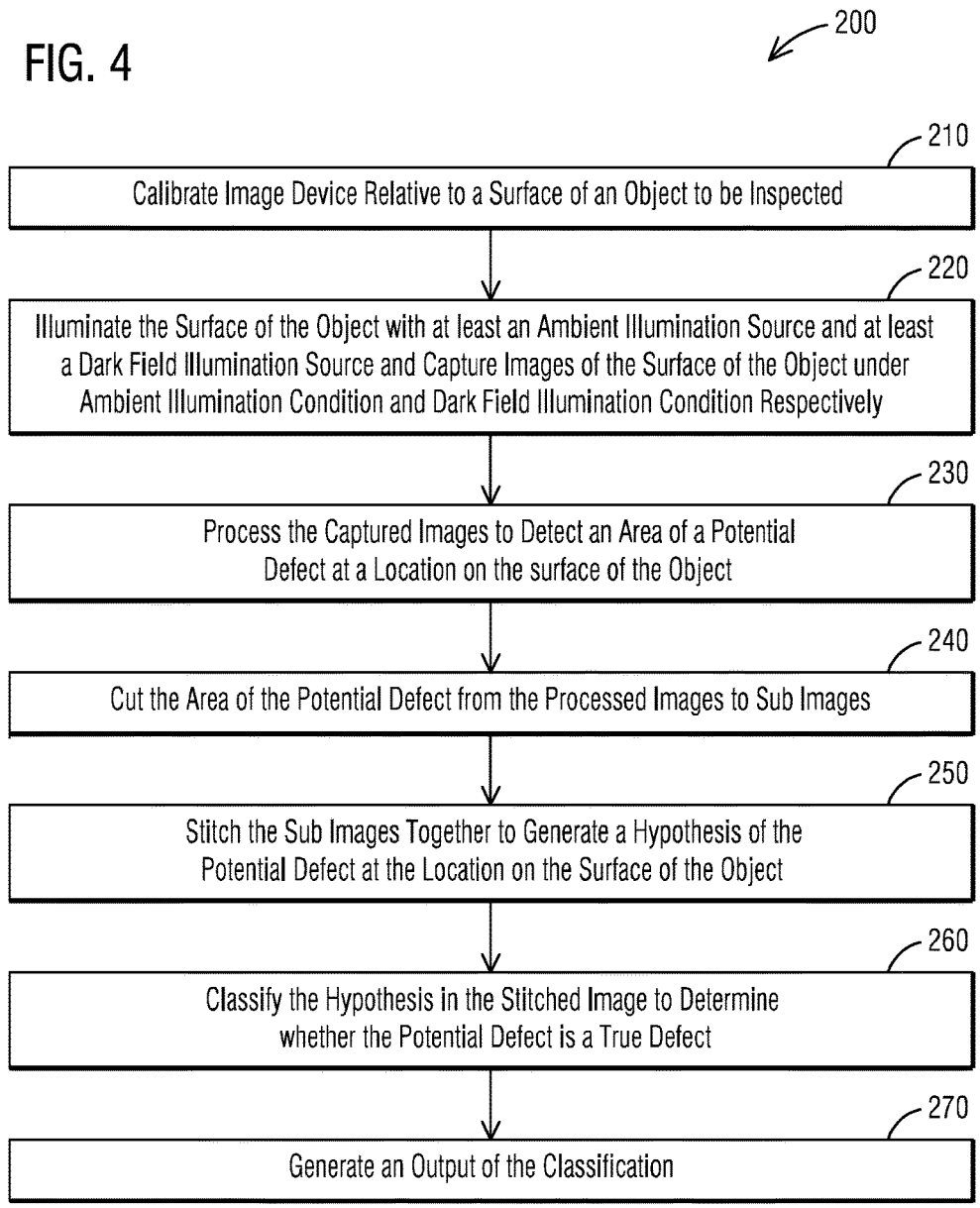
FIG. 4 illustrates a schematic flow chart of a method for detecting a defect at a surface of an object according to an embodiment of the invention.

FIG. 4 illustrates a schematic flow chart of a method 200 for detecting a defect at a surface 112 of an object 110 using an image processor 180 according to an embodiment of the invention. In step 210, the imaging device 140 may be calibrated relative to the surface 112 of the object 110 to be inspected. The calibration may estimate parameters of the lens 142 of the imaging device 140 to correct distortion of the lens 142 of the imaging device 140 when capturing images of the surface 112 of the object 110.

In step 220, the ambient illumination source 150 and the dark field illumination sources 160 may be triggered by the trigger controller 170 to illuminate the surface 112 of the object 110 with an ambient illumination condition and dark field illumination conditions. The imaging device 140 may be triggered by the trigger controller 170 to capture images of the surface 112 of the object 110 under the ambient illumination condition and the dark field illumination conditions respectively. Each image captures a field of view 144 of the surface 112 of the object 110 under different illumination conditions. Each image may contain potential defects having specific shapes on the surface 112 of the object 100. Shapes of the potential defects have predictable patterns consisting of bright region and shadow region based on configurations of the dark field illumination sources 160.

In step 230, the captured images of the surface 112 of the object 110 are processed by the image processor 180. The processing step 230 may implement a plurality of image operations to the captured images to detect areas of potential defects at locations on the surface 112 of the object 110. A plurality of areas may be detected having potential defects. Each area may have a potential defect. The locations of the plurality of areas may be represented by, such as x, y locations on a plane of the surface 112. The potential defects may be detected by patterns consisting of bright region and shadow region in the processed images. The plurality of image operations may enhance shapes of potential defects and reduce false detection rate.

In step 240, the areas showing the potential defects are cut off from the processed images to sub images. Size of each area to be cut off may be small enough to detect a micro defect. For example, size of each area may be less than 100 by 100 pixels, depending on resolution of the image. Areas that do not show indications of potential defects may be pruned out and do not need further processing.

In step 250, sub images having a potential defect at same location on the surface 112 of the object 110 are stitched together to generate a hypothesis of the potential defect at the location. A plurality of hypotheses of potential defects may be generated in a plurality of stitched images from sub images having potential defects at same locations on the surface 112.

In step 260, the stitched images are classified with a classifier to determine whether the potential defects are true defects on the surface 112 of the object 110. The classifier may be trained with a training data having characteristics of a true defect. According to an embodiment, a random forest classifier may be used to classify the potential defects. The random forest classifier may classify hypotheses with high efficiency and scalability in large scale applications.

In step 270, an output of the classification is generated. The output may include the detected true defects and the locations. The output may be a report form. The output may be an image with the detected true defects marked at the locations. The image may be one of the captured images or one of the processed images. The output may be stored in the imaging processor 180, or displayed on a display device 190, or print out by a printer.

Figure 5:
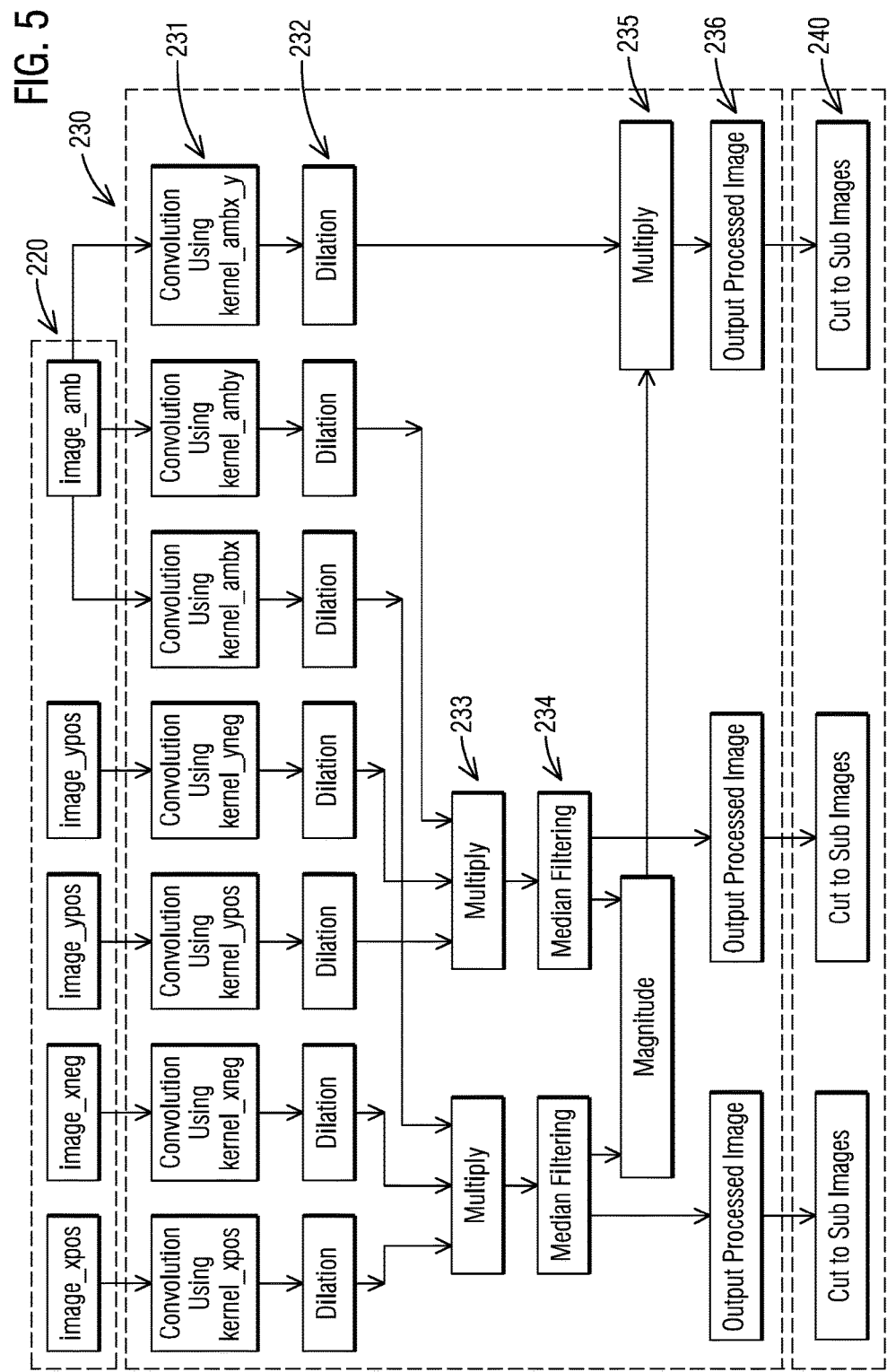
FIG. 5 illustrates a schematic flow chart of a step for processing images of the method as illustrated in FIG. 4 according to an embodiment of the invention.

FIG. 5 illustrates a schematic flow chart of a step 230 for processing images of the method 200 as illustrated in FIG. 4 according to an embodiment of the invention. Referring to FIG. 2 and FIG. 4 step 220, the trigger controller 170 may sequentially turn the ambient illumination source 150 and the dark field illumination sources 160 on and off. The trigger controller 170 may trigger the imaging device 140 to sequentially capture images of the surface 112 of the object 110 under ambient illumination condition and dark field illumination conditions respectively. The dark filed illumination sources 160 may be sequentially turned on and off by the trigger controller 170 so that images are sequentially captured by the imaging device 140 under sequential dark field illumination conditions. For example, image captured with the ambient illumination source 150 turned on is denoted as image_amb. Image captured with the dark field illumination source 160 located on x-positive position turned on is denoted as image_xpos. Image captured with the dark field illumination source 160 located on x-negative position turned on is denoted as image_xneg. Image captured with the dark field illumination source 160 located on y-positive location turned on is denoted as image_ypos. Image captured with the dark field illumination source 160 located on y-negative location turned on is denoted as image_yneg.

In step 231 of the step 230, convolution operations are implemented to the captured images with corresponding kernels. Convolution operations may filter noises in the captured images. Kernels are defined corresponding to predefined configurations of the dark field illumination sources 160 to enhance detecting a potential defect in the captured images based on a pattern consisting of bright region and shadow region under the predefined configurations of the dark field illumination sources 160. Shape of a potential defect, such as size or length of the potential defect, may have a specific and predictable pattern consisting of bright region and shadow region in an image under different configurations of the dark field illumination sources 160.

Different kernels affect output filtered images. For example, assuming color code as: black=1, white=0, grey=−1, the kernels for the five different images captured with certain predefined configurations of dark field illumination sources 160 may be defined as followings:

$$\text{kernel\_xpos} = \begin{bmatrix} -1 \\ -1 \\ -1 \\ -1 \\ -1 \\ 1 \\ 1 \\ 0 \\ 0 \\ 0 \\ 0 \end{bmatrix}, \text{kernel\_xneg} = \begin{bmatrix} 0 \\ 0 \\ 0 \\ 0 \\ 1 \\ 1 \\ -1 \\ -1 \\ -1 \\ -1 \\ -1 \end{bmatrix}, \text{kernel\_ambx} = \begin{bmatrix} 1 \\ 1 \\ 1 \\ -1 \\ -1 \\ -1 \\ -1 \\ -1 \\ 1 \\ 1 \\ 1 \end{bmatrix}$$

kernel_ypos = [kernel_xpos]$^T$ = [−1, −1, −1, −1, −1, 1, 1, 0, 0, 0, 0]

kernel_yneg = [kernel_xneg]$^T$ = [0, 0, 0, 0, 1, 1, −1, −1, −1, −1, −1]

kernel_amby = [kernel_ambx]$^T$ = [1, 1, 1, −1, −1, −1, −1, −1, 1, 1, 1]

kernel_ambx_y =

$$\begin{bmatrix} -0.1667 & -0.1667 & -0.1667 & -0.1667 & -0.1667 & -0.1667 \\ -0.1667 & -0.1667 & -0.1667 & -0.1667 & -0.1667 & -0.1667 \\ -0.1667 & -0.1667 & -0.1667 & -0.1667 & -0.1667 & -0.1667 \\ -0.1667 & -0.1667 & -0.1667 & -0.1667 & -0.1667 & -0.1667 \\ -0.1667 & -0.1667 & -0.1667 & -0.1667 & -0.1667 & -0.1667 \\ -0.1667 & -0.1667 & -0.1667 & -0.1667 & -0.1667 & -0.1667 \end{bmatrix}$$

Wherein: kernel_xpos is the convolution operator for image_xpos, kernel_xneg is the convolution operator for image_xneg kernel_ambx is the convolution operator for image_amb.
kernel_ypos is the convolution operator for image_ypos.
kernel_yneg is the convolution operator for image_yneg,
kernel_amby is the convolution operator for image_amb,
kernel_ambx_y is the convolution operator for image_amb.

The kernels may be redefined to detect potential defects in the captured images once configurations of the dark field illumination sources 160 changes, such as orientation, intensities, etc. The kernels are redefined based on different patterns of potential defects consisting of bright region and shadow region in the captured images under different configurations of the dark field illumination sources 160.

In step 232, dilation operations are implemented to the images filtered by the convolutions. Dilation operations are morphological operations that may probe and expand shapes of potential defects 112 in the filtered images using structuring elements. According to an embodiment, three-by-three flat structuring elements may be used in the dilation operations at step 232.

In step 233, multiply operations are implemented to the convoluted and dilated images. The multiply operations may further filter noises in the images. With reference to FIG. 4, images captured with dark field illumination sources 160 located at x-axis including image_xpos and image_xneg after operations of convolution using kernel_xpos and kernel_xneg respectively and dilations are multiplied with image_amb after operations of convolution using kernel_ambx and dilation to one image. Images captured with dark field illumination sources 160 located at y-axis including image_ypos and image_yneg after operations of convolution using kernel_ypos and kernel_yneg respectively and dilations are multiplied with image_amb after operations of convolution using kernel_amby and dilation to another image.

In step 234, median filtering operations are implemented to the multiplied images for further filtering the images. Median filtering operations may preserve potential defects 112 in the image while removing noises. The output images after median filtering operations may be detonated as image_x and image_y and may be output as two output images of imaging processing step 230.

In step 235, a magnitude operation is implemented to the two images image_x and image_y after the median filtering operations. Magnitude operation may maximize signal-to-nose ratio. The output image after magnitude operation is multiplied with image_amb after operations of convolution using kernel_ambx_y and dilation to one image detonated as image_xy.

In step 236, the processed images are output to three processed images of the imaging processing step 230. The three output processed images may include image_x, image_y, and image_xy. The three output processed images are enhanced from the captured images to detect areas of potential defects at locations on the surface 112 of the object 110. Areas of potential defects in each of the three output processed images are cut to sub images in step 240. With reference to FIG. 3, step 240 is then followed by step 250 and step 260.

According to an aspect, the proposed system 100 and method use a plurality of image processing techniques, such as image enhancement, morphological operation and machine learning tools including hypothesis generation and classification to accurately detect and quantify defects on any type of surfaces 112 of any objects 110 without relying on strong assumptions on characteristics of defects. The proposed system 100 and method iteratively prune false defects and detect true defect by focusing on smaller areas on a surface 112 of an object 110. The proposed system 100 and method may be used in power generation industry to accurately detect and quantify micro defects on surfaces of generator wedges. The micro defects may be a micro crack. The micro defects may be as small as micrometers, which is difficult to detect using traditional inspection methods.

According to an aspect, the proposed system 100 and method may be automatically operated by a computer to detect micro defects on a surface 112 of an object 110. The proposed system 100 and method may provide efficient automated micro defect detection on a surface 112 of an object 110. The proposed system 100 and method may provide a plurality of advantages in detecting micro defects on a surface 112 of an object 110, such as higher detection accuracy, cost reduction, and consistent detection performance, etc.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

REFERENCE LIST

100: System
110: Object
112: Surface of the Object
113: V-shaped Defect
114: First Portion of the V-shaped Defect
115: Bright Region
116: Second Portion of the V-shaped Defect
117: Shadow Region
120: Platform
122: Motor
124: Motor Controller
130: Hood
140: Imaging Device
142: Lens
144: Field of View
150: Ambient Illumination Source
160: Dark Filed Illumination Source
170: Trigger Controller
180: Image Processor
190: Display Device
200: Method

What is claimed is:
1. A method for detecting a defect on a surface of an object comprising:
supporting the object on a platform;

illuminating the surface of the object with a plurality of illumination sources comprising at least one ambient illumination source and at least one dark field illumination source;

capturing images of the surface of the object under illumination conditions with the illumination sources using an imaging device;

processing the captured images with a plurality of image operations using the image processor to detect an area of a potential defect at a location on the surface of the object;

cutting the area of the potential defect from the processed images to sub images using the image processor;

stitching the sub images together to generate a hypothesis of the potential defect at the location on the surface of the object using the image processor;

classifying the hypothesis in the stitched image with a classifier to determine whether the potential defect is a true defect using the image processor, wherein the classifier is trained with training data having characteristics of the true defect; and generating an output of the classification comprising the detected true defect and the location on the surface of the object.

2. The method as claimed in claim 1, wherein the potential defect comprises a pattern consisting of bright region and shadow region in the images.

3. The method as claimed in claim 1, wherein the processing step further comprises implementing convolution operations to the captured images using corresponding kernels.

4. The method as claimed in claim 3, wherein the kernels are defined corresponding to configuration of the dark field illumination source to detect the potential defect.

5. The method as claimed in claim 3, wherein the processing step further comprises implementing dilation operations to the convoluted images.

6. The method as claimed in claim 5, wherein the processing step further comprises multiplying the convoluted and dilated images to one image.

7. The method as claimed in claim 6, wherein the processing step further comprises implementing median filtering operations to the multiplied image, and wherein the median filtered image is the output processed image.

8. The method as claimed in claim 7, wherein the processing step further comprises implementing magnitude operation to the median filtered image.

9. The method as claimed in claim 8, wherein the processing step further comprises multiplying the magnitude image with one of the captured images under ambient illumination condition and processed with convolution and dilation operations, and wherein the multiplied image is the output processed image.

10. The method as claimed in claim 1, wherein the illumination sources are sequentially turned on and off.

11. A system for detecting a defect on a surface of an object comprising:

a platform for supporting the object;

a plurality of illumination sources comprising at least one ambient illumination source and at least one dark field illumination source for illuminating the surface of the object;

an imaging device for capturing images of the surface of the object under illumination conditions with the illumination sources; and an image processor for:

processing the captured images with a plurality of image operations to detect an area of a potential defect at a location on the surface of the object;

cutting the area of the potential defect from the processed images to sub images;

stitching the sub images together to generate a hypothesis of the potential defect at the location on the surface of the object;

classifying the hypothesis in the stitched image with a classifier to determine whether the potential defect is a true defect, wherein the classifier is trained with training data having characteristics of the true defect; and generating an output of the classification comprising the detected true defect and the location on the surface of the object.

12. The system as claimed in claim 11, wherein the potential defect comprises a pattern consisting of bright region and shadow region in the images.

13. The system as claimed in claim 11, wherein the processing operations comprise convolution operations to the captured images using corresponding kernels.

14. The system as claimed in claim 13, wherein the kernels are defined corresponding to configuration of the dark field illumination source to detect the potential defect.

15. The system as claimed in claim 13, wherein the processing operations comprise dilation operations to the convoluted images.

16. The system as claimed in claim 15, wherein the processing operations comprise multiplying the convoluted and dilated images to one image.

17. The system as claimed in claim 16, wherein the processing operations comprise median filtering operations to the multiplied image, and wherein the median filtered image is the output processed image.

18. The system as claimed in claim 17, wherein the processing operations comprise magnitude operation to the median filtered image.

19. The system as claimed in claim 18, wherein the processing step further comprises multiplying the magnitude image with one of the captured images under ambient illumination condition and processed with convolution and dilation operations, and wherein the multiplied image is the output processed image.

20. A computer program stored in a non-transitory computer readable medium and executable in a computer for performing a method of detecting a defect on a surface of an object, wherein the computer stores images of the surface of the object under illumination conditions with illumination sources comprising at least one ambient illumination source and at least one dark field illumination source, wherein the method comprises steps of:

processing the captured images with a plurality of image operations to detect an area of a potential defect at a location on the surface of the object;

cutting the area of the potential defect from the processed images to sub images;

stitching the sub images together to generate a hypothesis of the potential defect at the location on the surface of the object;

classifying the hypothesis in the stitched image with a classifier to determine whether the potential defect is a true defect, wherein the classifier is trained with training data having characteristics of the true defect; and generating an output of the classification comprising the detected true defect and the location on the surface of the object.

* * * * *